United States Patent [19]

Tantillo et al.

[11] 4,206,960

[45] Jun. 10, 1980

[54] ELECTRICAL CONNECTOR

[75] Inventors: James M. Tantillo, Brockton; Edward L. Boulanger, Hanson, both of Mass.

[73] Assignee: Component Manufacturing Service, Inc., West Bridgewater, Mass.

[21] Appl. No.: 893,291

[22] Filed: Apr. 5, 1978

[51] Int. Cl.[2] ........................ H01R 11/22; A61N 3/06

[52] U.S. Cl. .................................. 339/61 R; 339/261; 128/303.13

[58] Field of Search ................ 339/261, 255 B, 255 P, 339/75 R, 75 M, 61, 260, 253, 218 R; 128/303.13, 639-641, 783, 798, 802, 803

[56] References Cited

U.S. PATENT DOCUMENTS

| | | | |
|---|---|---|---|
| 1,039,279 | 9/1912 | Hammond | 339/261 |
| 1,044,885 | 11/1912 | Hammond | 339/261 |
| 1,086,820 | 2/1914 | Hammond | 339/261 |
| 1,195,079 | 8/1916 | Peterson | 339/261 |
| 1,291,297 | 1/1919 | Walas | 339/261 |
| 1,294,656 | 2/1919 | Hammond | 339/261 |
| 2,315,823 | 4/1943 | Smith | 339/260 X |
| 2,771,588 | 11/1956 | Schinske | 339/218 R X |
| 2,949,642 | 8/1960 | Lieberman | 339/218 R |
| 3,644,877 | 2/1972 | Carbonneau | 339/261 X |
| 3,704,439 | 11/1972 | Nelson | 339/217 R X |
| 3,740,703 | 6/1973 | Sessions | 339/255 P |
| 3,850,493 | 11/1974 | Clewes | 339/17 L X |

FOREIGN PATENT DOCUMENTS

| | | | |
|---|---|---|---|
| 292340 | 6/1928 | United Kingdom | 339/261 |

*Primary Examiner*—Joseph H. McGlynn
*Assistant Examiner*—John S. Brown
*Attorney, Agent, or Firm*—Wolf, Greenfield & Sacks

[57] ABSTRACT

An electrical connector for engaging a terminal stud has first and second insulating spring arms each carrying a conductive metal contact with the metal contacts defining through holes for electrically contacting a shank of a terminal stud. The metal contacts normally are in opposed spaced relationship to each other but are superimposed over each other and resiliently biased to their original position when the spring arms are squeezed toward each other by finger pressure. Release of the pressure causes the contacts to grasp the shank of a terminal stud over which the contacts are positioned.

An electrical connector is formed by positioning a preformed end piece over an insulated wire and then molding a plastic connector end in abutting relationship with at least a portion of said preform whereby the molding and forming temperature used does not adversely affect the insulation of said wire.

18 Claims, 10 Drawing Figures

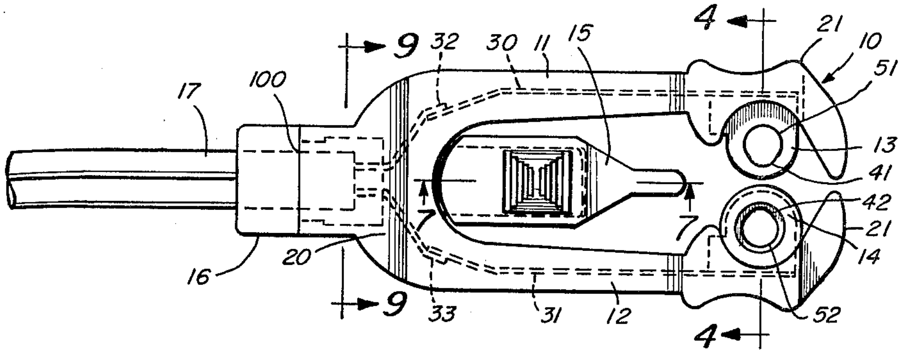
Fig. 1
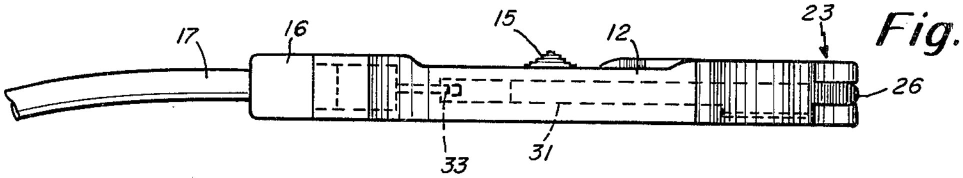
Fig. 2
Fig. 3
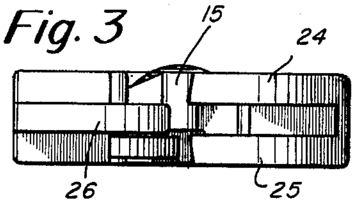
Fig. 4
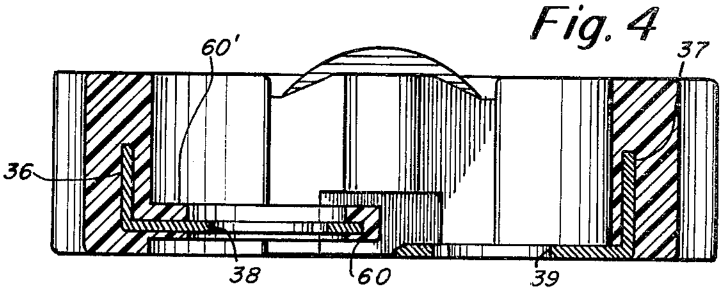
Fig. 5
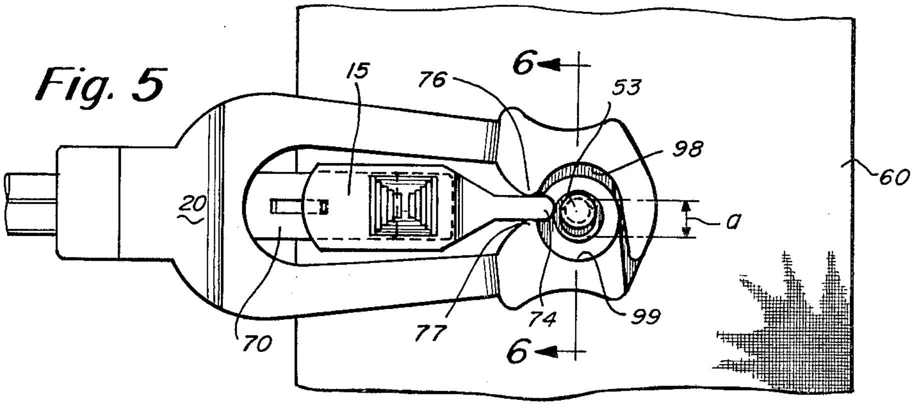
Fig. 7
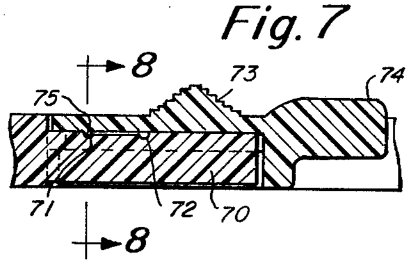
Fig. 6
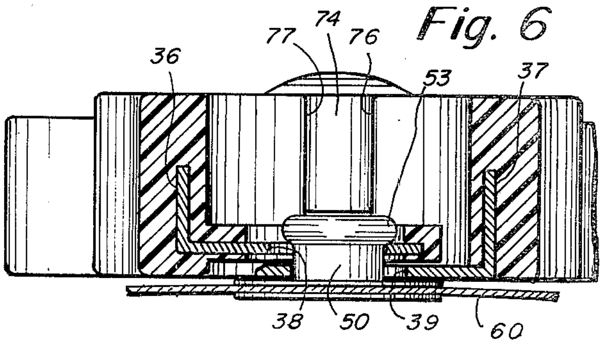

ELECTRICAL CONNECTOR

BACKGROUND OF THE INVENTION

A large variety of electrical connectors for connecting electrical wire to terminal studs are known in the art. Many of these connectors have arms which resilient bias portions of contacts against the shank of a terminal stud. For example the following patents generally disclose such connectors: British patent specification No. 198,471 dated June 7, 1923, U.S. Pat. Nos. 1,167,780; 1,201,109; 1,086,820; and U.S. Pat. No. 3,740,703. The present invention is an improved electrical connector which provides for positive mechanical interlocking with a terminal stud, excellent electrical contact and substantial failsafe features in a manner not suggested by the prior art.

The prior art noted above does not anticipate potential problems of molding plastic materials about an insulated wire to form an electrical connector. Often when an electrical wire is to be used as part of an integrally molded connector end, problems arise. These problems are sometimes connected with the fact that the polymeric material of connector to be molded and formed may have a higher molding or formation temperature than can be tolerated by the insulation of the wire. For example when the insulated wire has polyvinyl chloride insulation and the connector end is to be polycarbonate, difficulties are encountered in forming the connector end directly on the wire because of the high molding temperature of the polycarbonate which could damage the polyvinyl chloride.

SUMMARY OF THE INVENTION

It is an object of this invention to provide an electrical connector for engaging a terminal stud, which connector provides good electrical and mechanical contact with a stud in use and can be easily operated by the hand of a user.

It is another object of this invention to provide an electrical connector in accordance with the preceding object which permits two insulated wires to be connected to a stud through the connector while assuring that the wires are not placed in contact with each other except when connected to a stud.

Still another object of this invention is to provide an electrical connector in accordance with the preceding objects which has positive locking means to prevent inadvertent disengagement of the connector from a terminal stud to which it is engaged.

It is still another object of this invention to provide a method for forming an integrally molded connector end for an electrical connector in accordance with the preceding objects.

It is a still further object of this invention to provide a method of directly molding an integral polymeric connector end onto an insulated wire through the use of a preform which shields the insulated wire from molding temperatures encountered during a molding operation.

According to the invention an electrical connector for engaging a terminal stud has first and second opposed spring arms each carrying a conductive metal contact with each metal contact defining a through hole for electrically contacting a shank of a terminal stud. The metal contacts normally lie in opposed spaced relationship to each other in separate planes and are located to have the holes of each contact be superimposed over each other when the spring arms are squeezed together by finger pressure at positions adjacent the contacts. Release of pressure causes the contacts to grasp the shank of a terminal stud inserted into each of said holes. In the preferred embodiment the spring arms are made of a resilient plastic such as a polycarbonate which provides the spring bias of the arms. Preferably the holes are provided at opposed portions with dual radii so as to facilitate passage of the hole portions of the contacts over an enlarged head of a terminal stud, yet provide good mechanical and electrical engagement of a portion of the hole circumference with the shank of a terminal stud. The contacts are provided with insulating means for preventing accidental electrical contact of one with another except through the terminal stud. Positive locking means are provided to assure mechanical locking of the contact on a terminal stud to eliminate the possibility of accidental removal. Preferably alignment means act to provide positive alignment of the contacts with respect to each other in the operative position of the connector.

The features of the preferred embodiments of this invention make the electrical connector eminently suitable for use as a ground contact as in electrical surgery for connection to a grounding pad terminal stud. Positive electrical connection is important here to prevent extreme danger to the patient should the ground become inadvertently disconnected from the terminal stud.

BRIEF DESCRIPTION OF THE DRAWINGS

The above and other features, objects and advantages of the present invention will be better understood from a reading of the following specification in conjunction with the drawings in which:

FIG. 1 is a top plan view of a preferred embodiment of this invention;

FIG. 2 is a side view thereof;

FIG. 3 is a front plan view thereof;

FIG. 4 is a cross sectional view taken through line 4—4 of FIG. 1;

FIG. 5 is a top plan view showing the connector attached to a terminal stud;

FIG. 6 is a cross sectional view through line 6—6 of FIG. 5;

FIG. 7 is a cross sectional view through lines 7—7 of FIG. 1;

BRIEF FIGURE DESCRIPTION OF PREFERRED EMBODIMENTS

Figure 8:
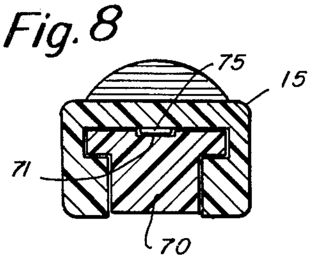
FIG. 8 is a cross sectional view through line 8—8 of FIG. 7.
Figure 9:
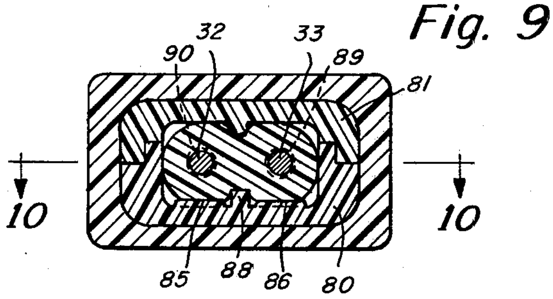
FIG. 9 is a cross sectional view through line 9—9 of FIG. 1.
Figure 10:
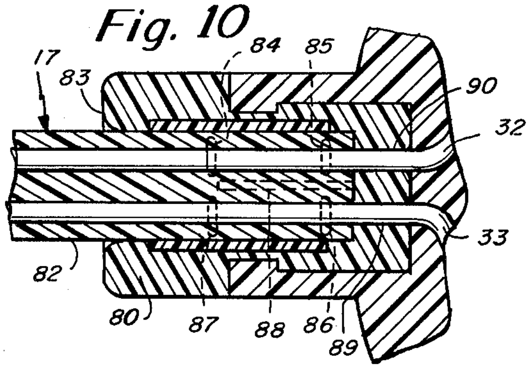
FIG. 10 is a cross sectional view through line 10—10 of FIG. 9.

With reference now to the drawings and more particularly FIGS. 1 and 2, an electrical connector is illustrated generally at 10 and has a pair of spring arms 11, 12 carrying contacts 13, 14 substantially at their ends. A slider locking means 15 is positioned between the arms. A preformed end piece section 16 acts as a strain relief and lead in for a two-wire insulated electrical line 17.

The arms 11 and 12 are preferably joined at an integral yoke section 20 and are integrally molded of a insulating polymeric material having resilient spring properties. For example polycarbonate can be used.

Udel Polysulfone a trademarked product of Union Carbide Corporation of New York, New York is paricularly suitable for use as the plastic or polymeric material of the connector. Enlarged, curved finger gripping portions 21, 22 are integrally formed with the arms and define an aligning means 23 at a forward end of the connector. The alignment means comprises integrally molded parallel fingers 24, 25 adapted to mate with finger 26 when the connector is in its closed position as shown in FIG. 5. These fingers when intermeshed, prevent misalignment or rocking of one arm with respect to the other and keep the arms in their proper planes during use even if significant twisting pressures are exerted on the connector.

The contacts 13 and 14 are preferably stamped metal contacts which are respectively interconnected with conductor arm portions 30, 31 which are in turn electrically connected with wires 32, 33 of the line 17. The material of the contacts can be spring metal to aid in enhancing the spring action of the arms.

The contacts 13 and 14 are preferably substantially planar portions having L-shaped ends 36 and 37 integral with portions 30, 31 and embedded in the arms. The planar portions define holes 38, 39 which holes have two radii as best seen in FIG. 1. The facing radii portions 41, 42 of contacts 13, and 14 respectively are such as to equal the radius of the shank 50 of an electrical terminal stud of known type as best shown in FIG. 6. The radius of each circumference portion 51, 52 of the contacts 13 and 14 is enlarged such that it enables ease of positioning the holes in superimposed alignment above the stud and passage of the contacts over the enlarged head 53 of the terminal stud. The small radii at 41, 42 are opposed to each other on the arms and grip opposite sides of the terminal stud closely conforming to the shank of the stud and providing good electrical and mechanical contact therewith.

The contacts 13, 14 are preferably insulated from each other at all times as by a safety layer of insulating plastic 60. Layer 60 acts as a spacer and prevents metal to metal contacting of the contacts even when they are in superimposed position. Thus, if a line monitor is on line 17 to determine when the contacts are in electrical engagement with each other, that monitor will only show engagement when the contacts are gripping a grounding stud as shown in FIGS. 5 and 6 since they cannot otherwise touch each other because of the positive blockage of the plastic layer 60. A layer 60' preferably covers the upper side of contact 14 to insulate the upper side.

The arms 11, 12 can be resiliently biased into the position shown in FIG. 5 by pressing with one's fingers at the finger grip portions. When the contacts are superimposed and slid down over the shank of a terminal stud as shown in FIGS. 5 and 6, the contacts tightly grip the stud, due to the spring action which urges the arms and contacts toward the original position of FIG. 1. The terminal stud can be of conventional design as known in the art for grounding and can for example comprise a base layer 60 which mounts a rivet-type, enlarged head stud as known in the art.

Once the contacts are in operative position and biased outwardly from the position shown in FIG. 5 toward their rest position as shown in FIG. 1, a locking means such as slide 15 is used to positively lock the connector to the terminal stud.

Slide 15 is mounted on a molded integral T-shaped extension 70 from the yoke 20. Extension 70 as best shown in FIG. 7, and 8 has detent means 71, 72. The slide has a button top 73 and a prong portion 74. The slide 15 moves under finger pressure from a first position shown in FIG. 7 with its detent 75 engaging detent 71, to and from a second position shown in FIG. 5 with its detent 75 engaging detent 72. In the forward position the prong 74 forms a physical abutment between projections 76, 77 on the inner sides of the arms 11 and 12, respectively. Thus, the arms cannot be forced closer together and cannot be removed from the terminal stud since they assume the position of FIG. 6. It is only after removal of the prong as by sliding of the slider 15 to its rearmost position shown in FIG. 7 that the arms can be moved further together, by pressure applied at the finger grip portions, to enable enlargement of the hole to the radii size of radii 51, 52 thus allowing clearance of the enlarged head 53, and removal of the connector from the terminal stud.

The rear end of the connector is formed by an end piece section 16 having two parts 80, 81 which are shell halves and which enclose the insulating jacket 82 of the two wire line 17. These preformed shell halves of the end piece section have a radius at 83 sufficient to form a strain relief for the line 17. In addition clamping ribs 84, 85, 86 and 87 are provided perpendicular to line 17 to clamp the insulation jacket. A longitudinally extending clamping rib 88 provides further mechanical locking action with the insulation jacket. The bare wires 32 and 33 extend out through closely surrounding through holes 89, 90 in each shell half 80, 81. The circumferences of the holes 89, 90 are such as to substantially prevent gas leakage into the mold during molding to prevent air bubbles in the molded piece. The tight fit about the conductors also prevents backup of the plastic into the end piece section 16.

The shell halves forming the end piece section are used to enable integral molding of the connector of this invention about the line 17. The end piece section formed by halves 80, 81 is preferably of a high temperature resistant material and can be hard rubber, thermosetting materials, thermoplastic materials, wood or other materials. The material is specifically selected to be resistant to the molding temperature of the polymeric material or plastic which is to be molded about the conductors and contacts to form the arms 11, 12. Polycarbonates can be used. The insulation of the line may be formed of an insulating polymeric material such as polyvinyl materials which have melting or distortion points such that material integrity would be damaged, as by deformation or deterioration, if exposed directly to the polycarbonate during the molding operation of the integrally molded connector end. Thus, the shell halves can be placed about the line end with the conductors 32, 33 extending therethrough. Preferably the shell halves are bound together as by ultrasonic welding or the use of suitable adhesives. The shell halves are then placed in a mold and completely block one wall of the mold which is cut out to have the end piece positioned therein. Line 100 may be at the side wall of a mold. The material of the arms 11 and 12 are then filled in the molding cavity at molding temperature with that material contacting only the metal wires and the preformed end piece section which is resistant to that molding temperature. Thus the molding temperature is never applied directly to the insulation of the line where it might adversely affect or damage the integrity of the line insulation. Interlock of the molded connector with the line is by a mechanical locking action of the shell halves with the line.

In a specific example of this invention, the line 17 is insulated with polyvinyl chloride and comprises two independent insulated conductor wires. The contacts 13, 14 each have holes which have dual radii of 0.093 to clear the stud head 53 and 0.055 inch to mate with the smaller radii of the terminal shank 50 and thus give good electrical contact with high reliability. The small radii helps to clean the stud during the clamping action as well as to give good mechanical surface contact. The shell halves 80, 81 are formed of polycarbonate (Lexan, a trademarked product of General Electric Company of Schenectady, N.Y.). Each arm has an overall length of about 2-¼inches and a substantially rectangular tapered cross section going from about 0.25"×0.14" at the yoke to 0.25"×0.115" at the finger grip section. The contacts are beryllium copper No. 25 heat treated for additional strength and have a stock thickness of 0.025 inch integrally formed with arm portions 30, 31 and planar portions defining the holes as previously described.

Connectors made in accordance with the present invention have substantial mechanical strength with good electrical contact properties. The alignment and locking means coact with the sliding locking means 15 to provide for locked engagement with a terminal stud and prevent accidental disconnection of the device once in place on a stud.

While a specific embodiment of this invention has been shown and described, many modifications are possible. For example the materials can vary as desired. While the slide locking means 15 is a preferred embodiment, it need not be used in all cases and similarly the alignment means 24, 25 and 26 can be eliminated if desired in certain embodiments. Alternative alignment and locking means are possible. For example, any means which prevents the arms from moving further toward each other once in the position shown in FIGS. 5 and 6, would act as a locking means for the device.

While it is preferred that a high temperature resistant insert end piece 16 be used as described, in some cases where the insulation of line 17 is not vulnerable to attack, the connector can be molded directly about the line insulation. In some cases an integral connector need not be used and a two-part housing can be formed. While in the preferred embodiment the resilient property of the arms is obtained by the polymeric material used for arms 11 and 12, in some cases spring means such as metal strips can be incorporated in the arms to provide substantially all of the resilient spring action.

While it is preferred to bond the shell halves 80, 81 prior to molding the connector end, in some cases no adhesive or separate bond need be used. In such cases the encircling molded body over a portion of the end piece 16 acts to hold the shell halves in position.

While the insulating feature insulating one contact from the other so that they can never move into the same plane is preferred, in some uses of the connector, it may be unnecessary. For example, when a single conductor wire is to be attached to a terminal stud using an electrical connector in accordance with this invention, the single wire can be passed to only one of the contacts. While polycarbonates are preferred for use in the connector, polypropylene, polyethylene, nylon and other materials can be used for the insulating polymers of the arms and connector body.

While the preferred contacts 13 and 14 define holes having an encircling rim completely thereabout, in some cases the holes can be formed by discontinuous edges as where the contact portion "a" noted in FIG. 5 is removed from each of the contacts. This and other discontinuous hole embodiments are not preferred when maximum mechanical strength is desired.

What is claimed is:

1. An electrical connector for engaging a terminal stud, said connector comprising, first and second opposed insulating spring arms each carrying a conductive metal contact each attached to an associated electrically isolated conductor of a line, each metal contact defining a through hole for electrically contacting a shank of an electrical terminal stud to electrically interconnect said electrically isolated conductors together, said metal contacts normally lying in opposed spaced relationship to each other and located to have said hole of each contact be superimposed on each other when said spring arms are squeezed together at positions adjacent said contacts, by pressure so that release of pressure causes resiliently biased gripping of a shank of a terminal stud inserted into said holes.

2. An electrical connector in accordance with claim 1 wherein said holes defined by said contacts each have two radii so as to provide for passage of said contacts over an enlarged head stud by the use of one radii of each hole and tight mechanical and electrical contact with said stud by the use of second radii.

3. An electrical connector in accordance with claims 1 or 2 wherein mating structural aligning means are provided for assuring substantially planar movement of said arms into contact with each other and preventing twisting of said arms with respect to each other.

4. An electrical connector in accordance with claims 1 or 2 and further comprising structural locking means for locking said arms in engagement with a terminal stud.

5. An electrical connector in accordance with claim 3 and further comprising structural locking means for locking said arms in engagement with a terminal stud.

6. An electrical connector in accordance with claim 4 wherein said locking means comprises a projection means interposed between said arms to prevent them from being moved closer towards each other.

7. An electrical connector in accordance with claim 5 wherein said locking means comprises a projection means interposed between said arms to prevent them from being moved closer towards each other.

8. An electrical connector in accordance with claim 6 or 7 wherein said projection means comprises a slider, depending from a yoke portion interconnecting said arms, for straight line reciprocal movement into and out of locking engagement with said arms.

9. An electrical connector in accordance with claims 1 or 2 and further comprising end piece means defining a strain relief and interconnecting said connector with an insulation covered electrical line formed of said conductors.

10. An electrical connector in accordance with claim 3 and further comprising end piece means defining a strain relief and interconnecting said connector with an insulation covered electrical line formed of said conductors.

11. An electrical connector in accordance with claim 4 and further comprising end piece means defining a strain relief and interconnecting said connector with an insulation covered electrical line.

12. An electrical connector in accordance with claim 9 wherein said end piece has a higher melting temperature than the insulation of said line.

13. An electrical connector in accordance with claim 10 wherein said end piece has a higher melting temperature than the insulation of said line.

14. An electrical connector in accordance with claim 11 wherein said end piece has a higher melting temperature than the insulation of said line.

15. An electrical connector in accordance with claim 12 further comprising said contacts each lying substantially in a plane, insulation means disposed between the plane of said first contact and said second contact whereby said contacts are positively insulated from each other at all times prior to contact with a terminal stud.

16. An electrical connector in accordance with claim 13 further comprising said contacts each lying substantially in a plane, insulation means disposed between the plane of said first contact and said second contact whereby said contacts are positively insulated from each other at all times prior to contact with a terminal stud.

17. An electrical connector in accordance with claim 14 further comprising said contacts each lying substantially in a plane, insulation means disposed between the plane of said first contact and said second contact whereby said contacts are positively insulated from each other at all times prior to contact with a terminal stud.

18. An electrical connector in accordance with claim 6 wherein said connector and the insulation of said electrical line are mechanically locked together.

* * * * *